(12) United States Patent
Ioulalen et al.

(10) Patent No.: US 6,572,892 B1
(45) Date of Patent: Jun. 3, 2003

(54) COSMETIC OR DERMOPHARMACEUTICAL COMPOSITION IN THE FORM OF BEADS AND METHODS FOR PREPARING SAME

(76) Inventors: Karim Ioulalen, 8 Avenue du Coustou, Saint Orens 31650 (FR); Rosanne Raynal, Avenue de Levezou, 12430 Villefrance de Panat (FR)

( * ) Notice: Subject to any disclaimer, the term of this patent is extended or adjusted under 35 U.S.C. 154(b) by 0 days.

(21) Appl. No.: 09/719,852

(22) PCT Filed: Jun. 16, 1999

(86) PCT No.: PCT/FR99/01445

§ 371 (c)(1),
(2), (4) Date: Mar. 19, 2001

(87) PCT Pub. No.: WO99/65448

PCT Pub. Date: Dec. 23, 1999

(30) Foreign Application Priority Data

Jun. 17, 1998 (FR) .............................. 98 07612

(51) Int. Cl.⁷ ............................ A61K 9/14; A61K 9/00; A61K 9/50
(52) U.S. Cl. ....................... 424/489; 424/400; 424/401; 424/502
(58) Field of Search ................................ 424/489, 400, 424/401, 502

(56) References Cited

U.S. PATENT DOCUMENTS 4,800,076 A * 1/1989 Bhat et al. .................... 424/69

6,262,034 B1 * 7/2001 Mathiowitz et al. ........ 424/468

FOREIGN PATENT DOCUMENTS

| EP | 0 720 845 | 7/1996 |
|----|-----------|--------|
| FR | 885 716 | 9/1942 |
| FR | 2 486 800 | 1/1982 |
| GB | 1 357 731 | 6/1974 |
| WO | 96 29056 | 9/1996 |

OTHER PUBLICATIONS

Vilivalam et al. "Development and evaluation of controlled–release diclofenac microspheres and tabetted microspheres", *J. Microencapsulation*, (1994), vol. 11, No. 4, pp. 455–470.

* cited by examiner

*Primary Examiner*—Thurman K. Page
*Assistant Examiner*—Robert M. Joynes
(74) *Attorney, Agent, or Firm*—Browdy and Neimark, P.L.L.C.

(57) ABSTRACT

The invention concerns an anhydrous solid composition comprising at least a hydrophobic wax, an oil and talcum, having preferably the form of beads with size ranging from 1 to 10000 microns. The beads can contain a cosmetic or pharmaceutical active principle, pigments or an agri-food constituent. The invention also concerns the method for preparing said beads.

20 Claims, No Drawings

COSMETIC OR DERMOPHARMACEUTICAL COMPOSITION IN THE FORM OF BEADS AND METHODS FOR PREPARING SAME

The present application is the national stage under 35 U.S.C. 371 of PCT/FR99/01445, filed Jun. 16, 1999.

This invention concerns a new type of bio-compatible pearl capable of containing various substances, biologically active constituents, cosmetic or pharmaceutical constituents, pigments or load products.

The use of active principles, or any compound or substance, for topical applications with a dermo-pharmaceutical or cosmetic purpose, requires incorporation into a support, referred to as a "base" for cosmetic applications and a "galenic support" for pharmaceutical applications.

This support has numerous functions:
- it must allow practical application at the administration point. In the case of local application with a cosmetic or dermo-pharmaceutical purpose, a fluid with an adapted rheologic behaviour is the form of support the most often chosen.
- it must allow the dilution of the active principle or the active compounds to obtain the desired concentration compatible with the effect sought.
- it must provide, in the case of cosmetic products, a feeling to the touch as agreeable as possible, and, in this case, the sensorial properties of the support are of primary importance.

The majority of cosmetic or dermo-pharmaceutical bases for topical applications are aqueous compounds, for example gels, lotions and emulsions. These cosmetic products are makeup removers, toning products, slimming gels, after-sun creams or lotions, capillary products, personal care products, tooth pastes and certain makeup products. Dermo-pharmaceutical compounds also use the such supporting bases.

These aqueous bases are today very widely used due to their high water content that gives, on application, a sensation of coolness on the skin and mucous. They leave no residue, do not shine and do not give a greasy aspect or feeling to the skin.

However, these aqueous bases, in particular, those in continuous aqueous phase, present a certain number of inconveniences recalled in patent FR 2 660554. Briefly, we note the drying effect of these bases on the skin, which is badly tolerated with dry or normal skin. The capacity of gels and emulsions to incorporate certain ingredients, such as essential oils or perfumes, without being destabilised, remains weak.

The bases of the emulsion type, containing a greasy phase, present a very creamy consistency. They are very much sought after since they are easily applied with the fingers from ajar or tube container (Patent FR 2734714). The great stability of these emulsions is due to the presence of waxes in the greasy phase whose melting point is generally higher than 80° C. Their preparation, at a temperature exceeding the wax melting point, prevents the use of thermo-sensitive active principles.

In addition to the drying effect observed, the aqueous phase is very favourable to the development of micro-organisms (Pharmacie galénic—Bonnes pratiques de fabrication des medicaments—A. Le Hir, Ed. Masson, page 88). Agents that limit the development of a wide spectrum of microbes must therefore be incorporated into these preparations. These agents, called preservatives, can be toxic for the skin of some people. Thus the use of certain preservatives is today highly regulated or even prohibited for some, for example diisobutyl-phenoxy-ethoxy-ethyl-dimethyl-benzylammonium, (Legislation et réglementations—Produits cosmétiques et produits d'hygiène corporelle—1997—page 229).

Finally, the water present in these cosmetic and dermo-cosmetic bases constitutes a very favourable environment for radical reactions and, in particular, oxidation reactions. Thus, the incorporation of molecules very sensitive to oxidative stress, such as vitamin C, certain fatty acids or certain polyunsaturated molecules, is very difficult due to low stability in time.

In the case of bases associating an aqueous phase and a lipidic phase, the essential presence of amphipilic molecules with surface-active powers allows stable dispersion and the blending of the two phases. These molecules may be rather aggressive for the skin (Les molecules de la beauté. De l'hygiène et de la protection pages 33–38, les tensioactifs, Pierre le Perchec, Ed. Nathan). We are therefore seeking to obtain anhydrous bases in which the active principles can be incorporated at temperatures less than 80° C. and whose texture is sufficiently creamy to allow satisfactory spreading with the fingers.

Anhydrous formulations destined for cosmetic and dermo-pharmaceutical applications have been known for a long time. The oldest are constituted from animal, vegetable, or mineral oils, or a blend of these. These oily forms are no longer used due to their greasy texture. Makeup bases in greasy phase are used above all because they adhere to the epidermis, provide protection and form a water-impermeable film. Anhydrous makeup products often come in a solid compact form, for example, lipstick, or in cream form (Peau-Soins cosmétioques et Préparations dermo-pharmaceutiques—R. Raoult, Ed. Porphyre page 106).

These bases, whilst interesting, are, nonetheless, very greasy and thick. On the one hand, their stability implies the presence of waxes whose melting temperatures, generally higher than 80° C., prevent the use of thermo-sensitive active principles.

An improvement is proposed in the French patent FR 2 734714, with the use in the base of an association of, in particular, organo-modified clay, polymer particles, pyro-genic silica dispersed in a greasy phase without the use of wax. This base, in anhydrous gel form, though still greasy is sufficiently creamy to be spread with the fingers. It can incorporate thermo-sensitive molecules. However, the clays used are modified by greasy quaternary ammonium salts that can be irritating for the skin. Finally, the greasy phase comprises oils of an amphiphilic nature, giving a shiny aspect to the skin.

After different studies, we have noted that the inconveniences of such previously used bases, that is to say:
- the drying effect, the presence of surface-active agents and antioxidants, the impossibility to use molecules sensitive to the oxidative stress in the case of aqueous bases,
- the greasy effect, the impossibility of using thermo-sensitive molecules, the shiny aspect and the difficulty of spreading for the anhydrous bases, could be solved by the use of pearls with a strictly anhydrous base and completely lacking surface active-agents, thus defining the invention.

Surprisingly, we have discovered that the association of oils, mineral waxes, animal or vegetable waxes, talc and silica, give a solid base, stable in time, able to contain active principles, offering a non-greasy, melting, film-forming, easy-to-spread texture without residues nor a shiny aspect.

However this base is not creamy enough to be easily taken with the fingers from ajar or tube container.

We have discovered that the particles prepared from this base, used alone, adhere sufficiently to the epidermis to be able to be taken easily with the finger and to be applied whilst retaining the properties of the base. We will give the name pearls to the particles resulting from the shaping of these bases. The base appears to be in a dispersed state, allowing topical cosmetic and dermo-pharmaceutical applications.

One of the aspects of this invention is that the base comprises at least one hydrophobic wax, a non amphiphilic oil and talc. The final melting temperature must be between 15° C. and 70° C., and preferably between 20° C. and 45° C.

The invention bases are mainly constituted from wax or blends of mineral waxes, non-greasy, non-amphiphilic mineral oils, talc and silica. They can contain, in addition, oily, paste or solid additives and liposoluble or hydrosoluble active ingredients.

The base generally contains from 0.1% to 40% of paraffin wax or a blend of paraffin wax and waxes chosen preferably from among:

Carnauba wax

Candelilla wax

Alfa wax ozocerite vegetable waxes such as olive wax, rice wax, hydrogenised jojoba wax or absolute flower waxes.

bees' waxes or modified bees' waxes.

It is possible to use other wax matrices, but the blend obtained must be characterised by a melting point of less than 90° C., by the absence of surface-active substances and a hydrophobic behaviour, and be non-wettable by water.

In the wax blend, paraffin wax represents, preferably, at least 40% of weight in relation to the total weight of the wax blend.

In addition to the waxes indicated above, the invention base generally contains a mineral oil or a blend of mineral oils, preferably a paraffin oil or a blend of paraffin oils and mineral oils, or synthetic oils chosen among:

hydrophobic silicone oils with viscosity of between 5 and 9000 centistokes and more particularly:

cyclomethicones lipophilic organofluorinated oils perhydrosqualen

In the oil blend, paraffin oil represents, preferably, between 4% and 90% in weight in relation to the blend. Other oily compounds, such as oleic alcohol, lanolin, sunflower oil, palm tree oil, can be used, but the oily blend obtained must be characterised by hydrophobic behaviour, must not be miscible in water and must have a melting point of between 0° C. and 45° C.

In addition to the oils and waxes indicated above, the invention base contains talc, sometimes with the addition of silica. We choose preferably a talc with a fine granule size, less than 5 micrometers and a pyrogenic silica that has not undergone any chemical derivation. The base generally contains 0.5% to 10% in weight of talc and silica particles. Moreover, it is possible to adjust the consistency by adding to the base, clays or their oily dispersions, phenylated silicon gums, starches and fatty structuring substances.

A particularly preferred form of the invented base also contains a polyoxyethylene glycol. Its addition allows the soft and melting qualities of the bases to be improved.

The invention bases are obtained by mixing at moderate heat. More precisely, these bases are obtained by a procedure characterised by mixing the wax and oil, at wax melting temperature, until obtaining a blend with a melting temperature less than the wax melting temperature. The initial relationship between the wax and the oil can be modulated so that the melting temperature of the final blend is less than the temperature at which the most heat-sensitive substance to be incorporated deteriorates. In practice, the percentage in weight of hydrophobic wax in the blend is between 1 and 40%. The final blend must be solid at room temperature and preferably have a melting temperature of 30° C. The blend is then cooled by adapted agitation, at a temperature 2° C. or 3° C. higher than its melting point, to allow the inclusion of the cosmetic or pharmaceutical active ingredients, silicon oils, polyoxyethylene glycols, talc and silica.

The compounds obtained are then shaped to give spherical hydrophobic particles called pearls.

One aspect of this invention is, therefore that it makes it possible to obtain an anhydrous base without emulsifying or surface-active agents. This invention also concerns a procedure for the preparation of pearls from bases as defined above.

The main techniques for preparing spheroid particles are mainly mechanical. For example, hot granulation around a solid core in a turbine or by a bed of fluidised air or in a planetary mixer, by passage through a channel, by moulding, by casting, or injection, hot or under pressure, in the moulds. These techniques have all the inconvenience of requiring important equipment and not allowing easy modulation of the size of the particles. The procedures are long and the base is subject to thermal, mechanical and oxidative stress, in the case of hot shaping under pressure.

The solvent evaporation technique, described in the patent FR 0 505 648, is based on the dispersion of an organic phase containing the constitutive products of the particles and the dispersing agents, in an aqueous non-miscible phase under agitation. This phase is followed by the elimination, without agitation, of the organic solvent under reduced pressure allowing the formation of particles. This method does not make it possible to obtain large-sized particles. Moreover, the complete elimination of the solvent is very difficult and finally, the particles obtained contain all or part of the dispersing agent.

The techniques based on extrusion and/or crushing imply the formation of particles with irregular surfaces and subject the base to thermal, mechanical and oxidative stresses.

Less aggressive techniques, or those that require little heating, exist for the treatment of substances sensitive to heat, oxidation, and mechanical stress. These are so-called cold solidification methods.

In the description of patent EP 0 438359, the cold blend containing the active ingredients and excipients, is dispersed in the form of droplets, by its passage through a nozzle, in a tower where they are cooled by a cold gas in counter flow, then recovered. Whilst this technique presents a clear improvement over the preceding techniques, it remains complex to implement, the dispersion stage is difficult to control and the size of the particles is not easily varied. We cannot obtain, or only with difficulty, particles whose size is greater than one millimetre. Finally, this technique does not allow large yields.

The techniques based on the cooling of the melted base, maintained in movement in a non-solvent liquid such as water, described in patents FR 2 705232, FR 2 660 534, EP 0 0435 008, are referred to as hot-melting techniques.

These techniques described by Langer (E. Mathiowcz and R. Langer, Journal of Controlled Release, 5. 1987, pages 13–22), consist in dispersing the compound or blend, previously melted, in a liquid heated to the same temperature, in which it is not miscible. The droplets obtained are solidified by cooling of the dispersion environment during agitation. As any professional will know, one of the great difficulties in these procedures is to obtain a good stabilisation of the emulsion produced. In fact, if the agitation is insufficient, the droplets tend to merge to reconstitute the two phases. The emulsion must be stabilised without variations in the size of the droplets until cooling at the solidification temperature. The size of the droplets depends on the speed of agitation, the viscosity of the dispersion environment and, of course, the presence of surface-active or emulsifying agents. In patents FR 2 658829 and EP 0 045008, the dispersion is stabilised by the presence of amphiphilic compounds allowing the stabilisation of the dispersion in aqueous phase and by maintaining important agitation. Whilst these procedures are interesting, they do not make it possible to obtain particles of sizes exceeding 1,000 micrometers and the elimination of surface-active agents remains very difficult.

In the description of patent FR 2 660554, the procedure does not call on the use of any emulsifying agent, since the lipidic base contains amphiphilic compounds allowing the dispersion to be stabilised in aqueous phase. It is not possible with such bases to prepare particles larger than 1000 micrometers by this procedure, and the particles thus prepared can hydrate and absorb up to eight times their weight in water. This procedure is therefore not compatible with strictly hydrophobic bases.

In the description of the patent FR 2 705232, the active ingredient is added to the hydrophobic polymer-based base at the time of the dispersion in an aqueous phase at a temperature exceeding the vitreous transition temperature. This procedure has the inconvenience of being long, since hot dispersion must be maintained until the end of the encapsulation of the active ingredients by the droplets.

This invention proposes a new procedure for the preparation of particles from bases part of the invention, in which the inconveniences of the techniques described in the preceding procedures can be avoided.

In comparison with the procedures of the aforementioned patents, the procedure of the present invention is carried out without using any emulsifying agent, solvent or pre-shaped particles and it is much more rapid. The particles obtained in this invention are spherical and between 1 and 10,000 micrometers in size. According to the invention's preferred method of realisation the pearls are between 1,000 and 10,000 micrometers in size and contain, dissolved or dispersed in their matrix, cosmetic, pharmaceutical or biotechnological ingredients. According to this method, the lipidic base of the pearls serves as a support and vehicle for ingredients such as perfumes, essential oils, aromas, pigments, loads, colorants, enzymes and coenzymes and other active cosmetic substances. The loading capacity of the pearls can vary from 0.02% to 75% in relation to the pearl weight.

As professionals will know, when we incorporate these constituents into the pearls, we must choose an appropriate lipidic base so that the procedure can be implemented, and that the pearls are solid at room temperature and preferably between 1,000 and 10,000 micrometers in size.

Among the cosmetic constituents that can be incorporated into the pearls we can cite vitamins or provitamins A, B, C, D, E, PP and their esters, hydrants, melanin, carotenoids, anti-radical substances, U.V. filters, keratolytic substances such as salicylic acid and its salts, molecules acting on pigmentation, inflammation, softening agents such as fatty esters, sebum substitutes or constituents, biological extracts, hair dyes, antiperspirants, molecules capable of trapping odours and aromas, so-called slimming molecules. Other constituents can be incorporated into the pearls, such as softening or lubricating substances for the skin, for example talc, kaolin, mica, nano-titanium, polyamide polymer microballs, or, to the contrary, powders destined for abrasion using particles of silica, or of polymer or plant origin.

The pearls can also contain preservatives, antioxidants, colorants and pigments along with dulling agents such as, for example, magnesium carbonate, stock, zinc power, zinc oxide, Toshiba Tospearl silicon blend micro-balls. We can incorporate into these pearls other microparticles or microcapsules, vector or matrix systems or substances containing active principles, cells and cell organites. Finally these pearls can contain pharmaceutical constituents destined to treat skin or mucous pathologies or capable of trans-dermal diffusion.

In this description, the term active constituent is used to refer to any active therapeutic substance or blend that can be beneficially administered to man or other mammal to diagnose, tend, reduce, treat or prevent disease. We can give the examples of antibiotics, hormones and derivatives, nicotine, anti-histamine agents, steroid and non-steroid anti-inflammatory agents, anti-allergic agents, local anaesthetics, vasodilators, anti-viral agents, antibodies and molecules acting on the immune system. This long list is not exhaustive.

In the case of oral administration of this type of particle, an appropriate base must be chosen, compatible in terms of toxicity, biocompatibility and bio-degradability with oral absorption. In this case the ingredients will be chosen from among the ingredients already used for oral administration and in such a way that the pearls formed retain their properties of incorporation and stabilisation of active constituents.

The pearls in this invention can contain mineral or organic pigments, including pearly pigments. Among the organic pigments, we can cite carbon black, varous D and C Red organic pigments, orange or yellow coded in the colour index. Among the mineral colorants, we can cite titanium dioxides, iron oxides, brown, black or yellow, chromium oxides, silicate of aluminium polysulphide ultramarine, manganese pyrophosphate, Prussian blue or ferric ferrocyanide. The pigments are present in the pearls in concentrations of between 0 and 30% and preferably between 1 to 20% in weight in relation to the pearl weight.

The pearls in this invention, loaded with pigments, can be used as base for makeup products such as foundations, complexion refiners, makeup correctors, tinted creams, eye shadow, blushers and lipsticks.

One aspects of the present invention is that it offers a procedure for preparing pearls containing pigments. The pearls containing pigments, prepared according to the invention procedure, can be used as a base for cosmetic products. In this preparation method, pearls can be less than 10 micrometers in size. In these conditions, the pearls can be used for the incorporation of pigments destined for the preparation of paints, inks and dyes.

This invention provides a new procedure for the preparation of particles called pearls in which the inconveniences of the techniques described in the procedures recalled above can be avoided.

In comparison with the hot melting techniques, the procedure of the present invention does not call on the intervention of emulsifying agents or amphiphilic products in the base to allow a stable dispersion at the time of the solidification by cooling phase. The blend of the different constituents and active principles forming the compound from which the pearls will be obtained is carried out in the first stage of the procedure. The mixing is carried out under heat, 2° C. or 3° C. above the melting points of the constituent presenting the highest melting point. As any professional will know, it is necessary to apply the agitation that is appropriate to the dispersion of all the constituents. Then the compound droplets are formed by dispersing the compound in a gel, previously heated to the same temperature, with which it is not miscible, with a sufficiently high viscosity to fix the dispersion. It is preferably to inject the compound within the gel, for example by a hole located at the base of the reactor. Agitation must be maintained throughout the injection and is carried out in an agitator system with blade equipped with an anchor, destined to disperse the compound, and a second axial blade equipped with a 3-blade propeller destined to form dispersion droplets of the desired size. This last stage is extremely rapid since the droplets are obtained gradually as the compound is injected. Agitation does not have to be maintained, since the droplets are fixed in the gel. At the end of injection, they are immediately cooled to the solidifying temperature then washed and recovered dry.

This procedure is therefore rapid and does not require any long and delicate agitation stage. It makes it possible to incorporate the active principles in the base right at the first phase of the mixing of the different compound products.

Among the gelling agents suitable for forming the gels used for the dispersion environment in the invention, we can cite carboxyvinyl polymers such as carbopols neutralised by soda, carrageen, polysaccharide thickeners and gelling agents such as xanthenes, guar and carob gums, alginates, cellulose, pectin and agar derivatives.

The gels used in the pearl preparation procedure have a concentration generally of between 0.1% and 50% in weight in relation to the total weight of the gel.

The pearls obtained are extremely homogeneous in size and can be manipulated industrially without special precautions. The following examples are not exhaustive—they are just to illustrate the invention

EXAMPLES

Example 1

Pearls Containing Pigments

Example for the manufacture of 100 g of pearls containing pigments

| Ingredients: | |
|---|---|
| Paraffin oil | 56 g |
| Paraffin | 15 g |
| Bees' wax | 2 g |
| Silicon oil | 5 g |
| Yellow iron oxide | 3 g |
| Red iron oxide | 2 g |
| Black iron oxide | 0.5 g |
| Titanium dioxide | 6 g |
| Talc | 5 g |
| Silica | 2 g |
| Parsol sun filter | 3 g |
| Perfume | 0.2 g |
| Preservative | 0.3 g |

Method

All the substances of the ingredients are hot mixed, in a thermostat recipient, at a temperature of 2° C. or 3° C. above the melting point of the constituent with the highest melting point. The most fragile constituents are added last. In the case where the constituents are not miscible in the base, these substances are dispersed in the the lipidic phase using a turbine at a speed of 100 rev/min. When the blend is homogeneous, it is added to 600 ml of aqueous carbol Ultrez 10 gel, neutralised at pH 6.5 with soda, previously heated to the same temperature as the blend and contained in a reactor quipped with a double anchor and 3-blade propeller agitation system. During the addition of the compound, the agitation speed of the anchor is 40 rev/min and the agitation speed of the 3-blade propeller is 135 rev/min. Agitation is maintained during 2 minutes after the end of the addition of the compound, then halted. The dispersion is then cooled to 15° C. The pearls are recovered by sifting, then washed in distilled water and recovered. The pearls thus obtained are 3 mm in size and can be used as makeup foundations.

Example 2

Pearls Containing Vitamins

| Ingredients | |
|---|---|
| Paraffin oil | 55 g |
| Paraffin | 16 g |
| Silicon oil | 6 g |
| Polyoxyethylene glycol 400 | 6 g |
| Talc | 6 g |
| Vitamin E | 0.5 g |
| Provitamin A | 0.3 g |
| Silica | 4 g |
| Titanium dioxide | 3 g |
| Sun filter | 3 g |
| Preservative | 0.2 g |

Method:

The method is identical to that described in example 1.

The pearls obtained are 3.5 mm in size and can be used for anti-age beauty products.

Example 3

Pearls Loaded with Essential Oils and Vegetable Oils

| Ingredients | |
|---|---|
| Liquid Vaseline oil | 62 g |
| Paraffin | 16 g |
| Bees' wax | 1 g |
| Silicon oil | 9 g |
| Sweet almond oil | 2 g |
| Essence of thyme | 0.5 g |
| Essence of marjoram | 0.5 g |
| Vitamin E | 0.5 g |
| Talc | 5 g |
| Kaolin | 1 g |
| Silica | 1 g |
| Perfume | 0.2 g |
| Preservative | 0.3 g |

Method

The method is identical to that described in example 1.

The pearls obtained are 3 mm in size and can be used to soothe and calm.

Example 4

Pearls Containing Sunscreen Products

| Ingredients | |
|---|---|
| Paraffin oil | 46 g |
| Paraffin | 22.8 g |
| Silicon oil | 10 g |
| Carnauba wax | 1 g |
| Lanolin | 1 g |
| Solécran sun filter | 6 g |
| Talc | 5 g |
| Silica | 1 g |
| Zinc oxide | 2 g |
| Titanium dioxide | 5 g |
| Preservative | 0.2 g |

Method

The method is identical to that described in example 1.

The pearls obtained are 4 mm in size and can be used in sun protection care.

Example 5

Pearls Containing a Pigment

| Ingredients: | |
|---|---|
| Paraffin oil | 69 g |
| Paraffin | 15 g |
| Carbon black | 8 g |
| Talc | 8 g |

Method

The method is identical to that described in example 1, except that the concentration in carbopol Ultez 10 is reduced to 1.1% in this example and the speed of agitation of the 3-blade propeller is 400 rev/min. The pearls loaded with pigments thus obtained are 25 micrometers in size and can be used in the ink, dye and paint industries.

Example 6

Pearls Loaded with Erythromycin

| Ingredients: | |
|---|---|
| Paraffin oil | 64 g |
| Vaseline oil | 18 g |
| Talc | 8 g |
| P.E.G. 300 | 4 g |
| Erythromycin base | 4 g |

Method

The method is identical to that described in example 1, except that the concentration in carbopol Ultez 10 is reduced to 3.8% in this example. The pearls loaded with erythromycin thus obtained are 2 mm in size and can be used for pharmaceutical applications linked to skin antibiotic treatment.

Example 7

Pearls Containing Vitamins

| Ingredients | |
|---|---|
| Palm oil | 32 g |
| Peanut oil | 10 g |
| Margarine | 43.8 g |
| Talc | 10 g |
| Vitamin E | 0.5 g |
| Vitamin C | 2 g |
| Preservative | 0.2 g |

Method

The method is identical to that described in example 1. The carbopol gel is replaced by a viscous solution with 2% of carob gum. The pearls obtained are 1 mm in size and can be used as a vitamin nutritional supplement.

Example 8

Pearls Containing Cells

| Ingredients | |
|---|---|
| Paraffin | 49 g |
| Vaseline oil | 6 g |
| Palm oil | 20 g |
| *Saccharomyces Cerevisiae dessique* | 20 g |
| Talc | 5 g |

Method

The method is identical to that described in example 1. The pearls containing the cells are 1 mm in size.

Example 9

Preparation of a Formulation Containing Pearls Loaded with Essential Oils to Obtain a Calming Gel

| | |
|---|---|
| Carbopol Ultez 10 | 0.15 g |
| Glycerine | 4 g |
| Lanoline | 4 g |
| Preservative | 0.3 g |
| Water q.s.p. | 100 g |

At room temperature 40 g of pearls loaded with essential oils obtained according to example 3 are incorporated into 60 g of this gel under agitation.

What is claimed is:

1. Base in the form of a solid hydrophobic blend,
    containing no water, surface-active agents, or emulsifying agents, and
    characterized by the fact that it comprises at least one hydrophobic wax, an oil and a talc,
    said talc being present in a maximum amount of 10% by weight based on the weight of said base in the form of a solid hydrophobic blend,
    said base in the from of a solid hydrophobic blend being a solid at ambient temperature.

2. Base according to claim 1 characterized by the fact that the final melting temperature must be no greater than 70° C.

3. Base according to claim 1 characterized by the fact that the oil used is an oil selected from the group consisting of the mineral oils, synthetic oils, silicone oils, fluorinated oils, plant oils and a blend of these.

4. Base according to claims 1, characterized by the fact that the hydrophobic wax is selected from the group consisting of:

Paraffin wax

Carnauba wax

Candelilla wax

Alpfa wax

Ozocerite

Vegtable waxes

Bees' wax and modified bees' wax and a blend of these.

5. Base according to claim 3, a characterised by the fact that the oil is a paraffin oil and the wax is a paraffin wax.

6. Base according to claim 1, characterised by the presence of silicon oil, polyoxyethylene glycol 300 and silica as additives.

7. Procedure for the preparation of anhydrous and hydrophobic pearls with a spherical shape comprising a lipidic hydrophobic matrix with a melting point of above ambient temperature and no greater than 70° C., substantially free of water, surface active agent and emulsifying agent, that can contain at least one active ingredient, the said procedure comprising the following stages:

the different constituents and active principle are hot mixed at 2° C. or 3° C. above the melting point of the ingredient presenting the highest melting point;

dispersion by injection when the blend is under agitation in a gel previously heated to the same temperature, with which it is not miscible, and with a sufficiently high viscosity to fix the dispersion of pearls formed;

halting of the agitation at the end of the injection and cooling of the dispersion below the temperature for the solidification of the pearls;

recovery and washing of the anhydrous and hydrophobic pearls.

8. Procedure according to claim 7, characterised by the fact that the addition of the blend is carried out by injection during agitation at the lower part of the recipient containing the gel.

9. Procedure according to claim 7, characterised by the fact that the agitation of the gel during injection is obtained using a blade equipped with an anchor and a coaxial blade equipped with propeller.

10. Procedure according to claim 7, characterized by the fact that the gel is prepared from gelling agents selected from the group consisting of carboxyvinyl polymers, carrageen and polysaccharide thickeners, xanthenes, guar and carob gums, alginates, cellulose derivatives, pectin, and agar.

11. Procedure according to claim 7, characterised by the fact that the gel presents a concentration in gelling agent of between 0.1% and 50% in weight in relation to the total gel weight.

12. Pearls characterised by the fact that they are prepared according to procedures of claim 7.

13. Pearls characterised by the fact that they are prepared from a base of claim 1.

14. Pearls according to claim 12, characterised by the fact that they are between 1 and 10,000$\mu$ in size.

15. Pearls according to claim 12, characterised by the fact that they contain one or several active cosmetic or pharmaceutical constituents soluble or not in the pearls.

16. Pearls according claim 12, characterized by the fact that they contain at least one active cosmetic or pharmaceutical constituent selected from the group consisting of:

the vitamins or provitamins A, B, C, D, E, PP and their esters, moisturizers, melanin, carotenoids, anti-radical substances, hydroxyacids, antiseptics, anti-acne agents, antidandruff agents, U.V. filters, keratolytics, molecules acting on pigmentation or on inflammation, softening agents, biological extracts, hair dyes, antiperspirants, molecules capable of trapping odours and aromas, softening or lubricating agents for the skin, powders destined for abrasion using particles of silica either with a polymer or plant origin component, preservatives, antioxidants, colorants and pigments along with dulling agents, vector or matrix systems containing active principles, cells and cell organites, antibiotics, hormones and derivatives, anti-allergic agents, local anaesthetics, vasodilators, anti-viral agents, anti-bodies and molecules acting on the immune system.

17. Pearls according to claim 12, characterised by the fact that they contain a pigment used for the preparation of inks, paint and dyes.

18. Cosmetic or dermo-pharmaceutical base characterised by the fact that it contains pearls according to claim 12, in suspension in the continuous phase.

19. Pearls according to claim 16, wherein the final melting temperature is not less than 30° C., and comprising as said wax wither a paraffin wax or a mixture of paraffin wax with at least one other wax, and wherein said composition comprises 0.1% to 40% of said wax or waxes, and further wherein paraffin wax comprises at least 40% of the total of said waxes.

20. Pearls according to claim 19 having a size between 1 and 10,000$\mu$ and wherein said at least one active cosmetic or pharmaceutical constituent is selected from the group consisting of said vitamins or provitamins and their esters, said moistureizers, said melanin, said carotenoids, said anti-radical substances, said hydroxyacids, said antiseptics, said anti-acne agents, said antidandruff agents, said UV filters, salicylic acid and its salts, said molecules acting on pigmentation or inflammation, fatty esters, sebum constituents or substitutes, said biological extracts, said hair dyes, said antiperspirants, said molecules capable of trapping odors and aromas, kaolin, mica, nano-titaniums, polyamide polymer micro-balls, said powders destined for abrasion using particles of silica either with a polymer or plant origin component, said preservatives, said antioxidants; said colorants and pigments along with at least one of magnesium carbonate, starch, zinc powder, zinc oxide, silicon-blend micro-balls, micro-particles or micro-capsules, said vector or matrix systems containing said active principles, said cells and said cell organites, said antibiotics, said hormones and derivatives, said anti-allergic agents, said local anaesthetics, said vasodilators, said anti-viral agents, said anti-bodies and said molecules acting on the immune system.

* * * * *